(12) United States Patent
Pilar et al.

(10) Patent No.: US 11,352,720 B2
(45) Date of Patent: Jun. 7, 2022

(54) DEVICE FOR CONTACTLESS MEASUREMENT OF THE PARAMETERS OF A LINEAR TEXTILE FORMATION, A METHOD OF CONTROLLING THE DEVICE AND A TEXTILE MACHINE

(71) Applicant: Maschinenfabrik Rieter AG, Winterthur (CH)

(72) Inventors: Evzen Pilar, Litomysl (CZ); Bernd Bahlmann, Schrobenhausen (DE)

(73) Assignee: Maschinenfabrik Rieter AG, Winterthur (CH)

( * ) Notice: Subject to any disclaimer, the term of this patent is extended or adjusted under 35 U.S.C. 154(b) by 381 days.

(21) Appl. No.: 16/277,067

(22) Filed: Feb. 15, 2019

(65) Prior Publication Data

US 2019/0249339 A1   Aug. 15, 2019

(30) Foreign Application Priority Data

Feb. 15, 2018  (CZ) .................................. CZ2018-75

(51) Int. Cl.
  *D01H 13/26*  (2006.01)
  *G01N 21/89*  (2006.01)
(52) U.S. Cl.
  CPC ......... *D01H 13/26* (2013.01); *G01N 21/8915* (2013.01)
(58) Field of Classification Search
  None
  See application file for complete search history.

(56) References Cited

U.S. PATENT DOCUMENTS

| | | | | |
|---|---|---|---|---|
| 4,970,402 | A | * | 11/1990 | de Vuyst .............. B65H 63/065 250/559.12 |
| 5,194,911 | A | * | 3/1993 | Stutz ...................... D01G 23/06 19/0.23 |
| 7,057,197 | B2 | | 6/2006 | Stusak |
| 7,333,202 | B2 | * | 2/2008 | Birlem ............... G01N 21/8915 356/429 |
| 8,400,503 | B2 | | 3/2013 | Linnenkohl et al. |
| 10,816,534 | B2 | * | 10/2020 | Werheit ............... G01B 11/105 |

(Continued)

FOREIGN PATENT DOCUMENTS

| | | |
|---|---|---|
| CZ | 298 929 B6 | 3/2008 |
| CZ | 299 647 B6 | 10/2008 |

(Continued)

OTHER PUBLICATIONS

CZ Search Report, dated Nov. 16, 2018.
EPO Search Report, dated Jun. 28, 2019.

*Primary Examiner* — Peter J Macchiarolo
*Assistant Examiner* — Jermaine L Jenkins
(74) *Attorney, Agent, or Firm* — Dority & Manning, P.A.

(57) ABSTRACT

A device for contactless measurement of one or more parameters of a linear textile formation (e.g., yarn) includes a yarn sensor with at least two mutually independent detection zones for one or a combination of the parameters of yarn presence, yarn movement, or yarn quality. The individual detections zones are arranged in defined positions relative to at least two different yarn paths of the yarn at a workstation depending on changed states of the yarn at the workstation so that at least one of the parameters is measured in each of the detections zones.

18 Claims, 5 Drawing Sheets

(56) References Cited

U.S. PATENT DOCUMENTS

2004/0051058 A1\* 3/2004 Stusak ............... G01N 21/8915
250/559.27
2019/0025156 A1\* 1/2019 Takahashi .............. G02B 6/448

FOREIGN PATENT DOCUMENTS

| CZ | 305 558 B6 | 12/2015 |
|----|------------|---------|
| DE | 38 34 110 A1 | 4/1990 |
| DE | 10 2014 211249 A1 | 12/2014 |
| EP | 2 573 217 A2 | 3/2013 |
| GB | 2 423 528 A | 8/2006 |
| WO | WO 99/36746 A1 | 7/1999 |
| WO | WO 02/37056 A1 | 5/2002 |
| WO | WO 2007/010325 A1 | 1/2007 |

\* cited by examiner

DEVICE FOR CONTACTLESS MEASUREMENT OF THE PARAMETERS OF A LINEAR TEXTILE FORMATION, A METHOD OF CONTROLLING THE DEVICE AND A TEXTILE MACHINE

TECHNICAL FIELD OF THE INVENTION

The invention relates to a device for contactless measurement of the parameters of a linear textile formation, such as yarn, thread, fibers, sliver, etc., with a yarn sensor.

The invention also relates to a method of controlling the device for contactless measurement of the parameters of a linear textile formation, such as yarn, thread, fibers, sliver.

In addition, the invention also relates to a yarn manufacturing textile machine comprising, at each workstation, the device for contactless measurement of the parameters of a linear textile formation.

BACKGROUND

Devices for contactless measurement of the parameters of a linear textile formation, e.g., such as yarn, thread, fibers, sliver, etc., are known in the prior art. These devices comprise a radiation source and a sensor of radiation consisting of a system of radiation sensitive elements connected to an evaluation device and providing information about the monitored parameters of the linear textile formation.

WO 99/36746 discloses a device for contactless measurement of the parameters of a linear textile formation comprising a CCD optical sensor. However, the disadvantage is a relatively high price of the sensor and limited sensing speed, especially with matrix arrangement of the radiation sensitive elements of the sensor on the required area.

CZ 298929 B6 and CZ 299647 B6 describe devices for contactless measurement of the parameters of a linear textile formation which comprise a CCD optical sensor having a plurality of radiation sensitive elements arranged at least in one row. The advantage of these solutions is a lower cost and higher sensing speed.

The common disadvantage of the known solutions is the fact that the linear textile formation is measured in one region of the workstation of the machine, and so the information about the measured formation is only provided from that one region.

An aim of the invention is to extend the possibilities of using the device for contactless measurement of the parameters of a linear textile formation, to allow obtaining further information about the monitored linear textile formation and to use this further information to control the machine or the workstation.

SUMMARY OF THE INVENTION

Additional objects and advantages of the invention will be set forth in part in the following description, or may be obvious from the description, or may be learned through practice of the invention.

An aim of the invention is achieved by a device for contactless measurement of the parameters of a linear textile formation, such as yarn, thread, fibers, sliver, etc., whose principle consists in that a yarn sensor is provided with at least two mutually independent detection zones of the presence and/or quality and/or movement of yarn, the individual detection zones being arranged in defined positions relative to the yarn path in different situations and states of yarn at the workstation.

The principle of the method of controlling the device for contactless measurement of the parameters of a linear textile formation, such as yarn, thread, fibers, sliver, which comprises a yarn sensor, consists in that the individual detection zones are activated or deactivated depending on the current activity at the workstation.

The principle of the yarn manufacturing textile machine consists in that it comprises the device according to the invention at each workstation.

The advantage of this solution is the fact that each detection zone of the yarn sensor detects separately the state of yarn or changes thereof, that is, the state of the yarn path or changes thereof, the state of the speed of the yarn movement or changes thereof, etc., and passes this information to a control unit which, according to a pre-programmed decision algorithm for the determined operating procedure, evaluates the detected state and/or changes thereof and makes a decision about the next operating procedure at the workstation. The device may be advantageously used, for example, to determine the follow-up steps after the yarn reserve from a temporary (vacuum) yarn storage device is consumed during the resumption of the yarn spinning process on a spinning textile machine and it is necessary to start a yarn loop compensation on a yarn winding device and resume the operation of a spinning unit and a draw-off mechanism, etc.

BRIEF DESCRIPTION OF DRAWINGS

The invention is schematically illustrated in the drawing, where:

FIG. 6b shows a spatial representation of the exemplary embodiment of FIG. 6, and FIG. 6a.

DETAILED DESCRIPTION

Figure 1:
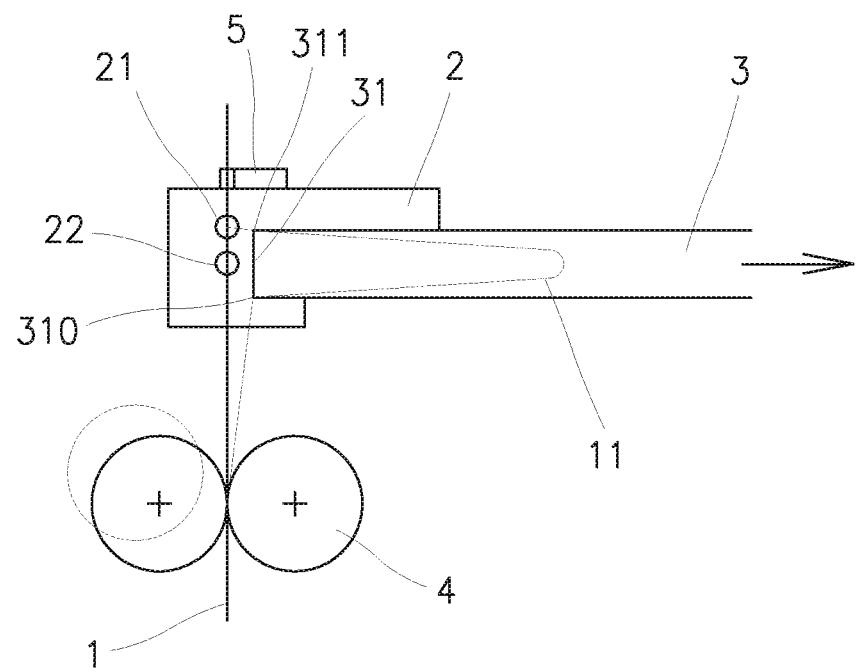
FIGS. 1 to 5 show different configurations of detection zones of the device for contactless measurement of the parameters of a linear textile formation according to the invention, e.g., yarn, thread, fibers, fiber sliver, etc., relative to the temporary yarn storage device at the workstation of a textile machine.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

The invention will be further described with reference to an exemplary embodiment of the method for contactless measurement of the parameters of a linear textile formation, such as yarn, thread, fibers, sliver, etc.; at the workstation of a textile machine and with reference to an exemplary embodiment of the device for contactless measurement of the parameters of the linear textile formation.

A textile machine, e.g., a yarn manufacturing spinning machine, comprises at least one row of identical workstations arranged next to each other. The workstations are well-known as such and therefore only the relevant nodes will be described hereinafter. Each workstation comprises an unillustrated spinning unit in which yarn 1 is formed. A yarn draw-off mechanism 4 of is located above the spinning unit. The draw-off mechanism 4 comprises a pair of draw-off rollers, which are rotatably mounted in the machine structure, whereby one of the draw-off rollers is coupled to an unillustrated drive and constitutes a driven draw-off roller, while the other draw-off roller is rotatably mounted on a swinging spring-loaded arm and constitutes a pressure draw-off roller. Thus, in the working position, the two draw-off rollers are situated above each other and at the point of their contact there is a pressing line through which passes the yarn 1 which is withdrawn from the spinning unit while the draw-off rollers are rotating. Above the draw-off mechanism 4 is situated a temporary (vacuum) yarn storage device 3 whose suction inlet 31 is situated near the yarn path between the draw-off mechanism 4 and a yarn winding device (which is not shown and will be mentioned hereinafter) on an unillustrated bobbin. This suction inlet 31 of the temporary storage device 3 is, in the shown exemplary embodiment, associated with a yarn sensor 2 according to the invention with at least two mutually independent yarn detection zones 21 and 22, to detect the yarn 1 at two different points of its working path by one sensor 2. In the direction of the yarn movement, the yarn winding device (not shown) with a yarn traversing device is arranged behind the suction inlet 31 of the temporary storage device 3 and, if appropriate, before the suction inlet 31 is arranged a device for the compensation of a loop of yarn 1 wound on the cross-wound bobbin in the winding arms of the winding device.

FIG. 1 schematically illustrates a part of the workstation in the region of the temporary vacuum storage device 3 of yarn 1 in the state before the start of the production activity at the workstation, when the yarn 1 is guided from the spinning unit and passes freely between the mutually spaced apart draw-off rollers of the draw-off mechanism 4 and is introduced into the temporary storage device 3, in which a yarn reserve 11 is formed by the vacuum. From the temporary storage device 3 the yarn 1 further passes towards the other working elements of the workstation, namely to a yarn guide 5, the yarn traversing device, and the yarn winding device (not shown). The yarn path is in the region of the inlet 31 of the temporary yarn storage 3 associated with the yarn sensor with a pair of detection zones 21, 22, which are arranged above each other, whereby the two detection zones 21, 22 are assigned to a straight yarn path (full line of the yarn 1—the yarn 1 does not pass through the temporary storage device 3) before the inlet 31 of the temporary yarn storage device 3. At the same time, however, the upper detection zone 21 of the sensor 2 is assigned to the deflected yarn path (dashed line of yarn 1) when the yarn 1 at the workstation passes through the temporary storage device 3. In this situation, when the yarn 1 at the workstation passes through the temporary storage device 3 (dashed line of the yarn 1), the lower detection zone 22 is assigned to the region above of the yarn inlet 1 into the temporary storage device 3. As a result, in this situation when the yarn 1 at the working station passes through the temporary storage device 3, the yarn 1 passes outside the lower detection zone 22. In other words, the lower detection zone 22 is situated outside the deflected yarn path passing through the temporary storage device 3. The invention then operates in such a manner that during the resumption of the manufacturing process at the workstation of the machine, when the yarn 1 is sucked into the temporary storage device 3 (dashed line of yarn 1), the unillustrated winding device starts to wind the yarn 1 on a yarn bobbin, consuming the yarn reserve 11 from the temporary storage device 3. After consuming this yarn reserve 11 from the temporary storage device 3 the yarn 1 is completely withdrawn from the temporary storage device 3 the working yarn path is straightened (it changes from the deflected path indicated by a dashed line to a straight path indicated by a solid line) and extends to the lower detection zone 22 of the yarn sensor 2. Hereby, the control unit of the workstation (or of the section of the workstations or of the machine) receives the information that the yarn 1 has left the temporary storage device 3 and it adjusts accordingly the subsequent operating activity of the workstation to put the workstation into full production mode.

Figure 2:
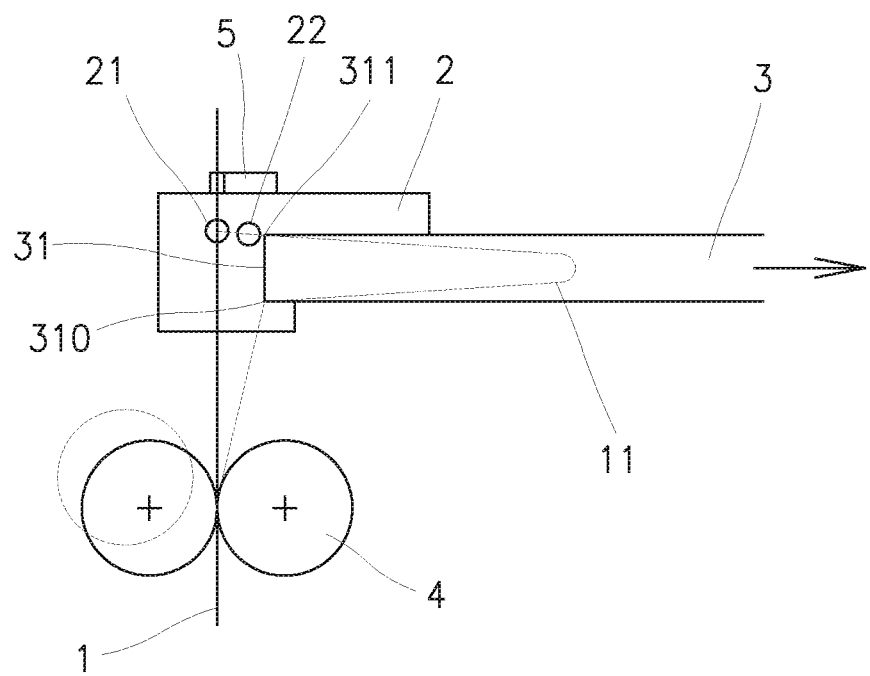

FIG. 2 schematically illustrates a part of the workstation, as in FIG. 1, whereby the yarn sensor 2 has two detection zones 21 and 22, which are assigned to the working yarn path in the region of the inlet 31 of the temporary storage device 3. In particular, the upper detection zone 21 is assigned to the straight yarn path 1 (solid line of yarn 1—the yarn 1 does not pass through the temporary storage device 3) and at the same time it is associated also with the deflected yarn path (dashed line of yarn 1) in the region of the outlet of yarn 1 from the temporary storage device 3. The lower detection zone 22 is assigned only to the deflected yarn path (dashed line of yarn 1) in the region of the outlet of yarn 1 from the temporary storage device 3, when the yarn 1 at the workstation passes through the temporary storage device 3. In this situation, when the yarn 1 at the workstation passes through the temporary storage device 3, the yarn 1 passes at first through the lower detection zone 22 and then also through the upper detection zone 21. The invention then operates in such a manner that during the resumption of the manufacturing process at the workstation of the machine, when the yarn 1 is sucked into the temporary storage device 3 (dashed line of yarn 1), the unillustrated winding device starts to wind the yarn 1 on the yarn bobbin, consuming the yarn reserve 11 from the temporary storage device 3. After consuming the yarn reserve 11, the yarn 1 is completely withdrawn from the temporary storage device 3 the working yarn path is straightened (changing from the deflected path indicated by a dashed line to a straight path indicated by a solid line), and the yarn 1 leaves the lower detection zone 22 of the yarn 1 sensor 2. Hereby, the control unit of the workstation (or of the section of the workstations or of the machine) receives the information that the yarn 1 has left the temporary storage device 3, and it adjusts accordingly the subsequent operating activity of the workstation to put the workstation into full production mode.

Figure 3:
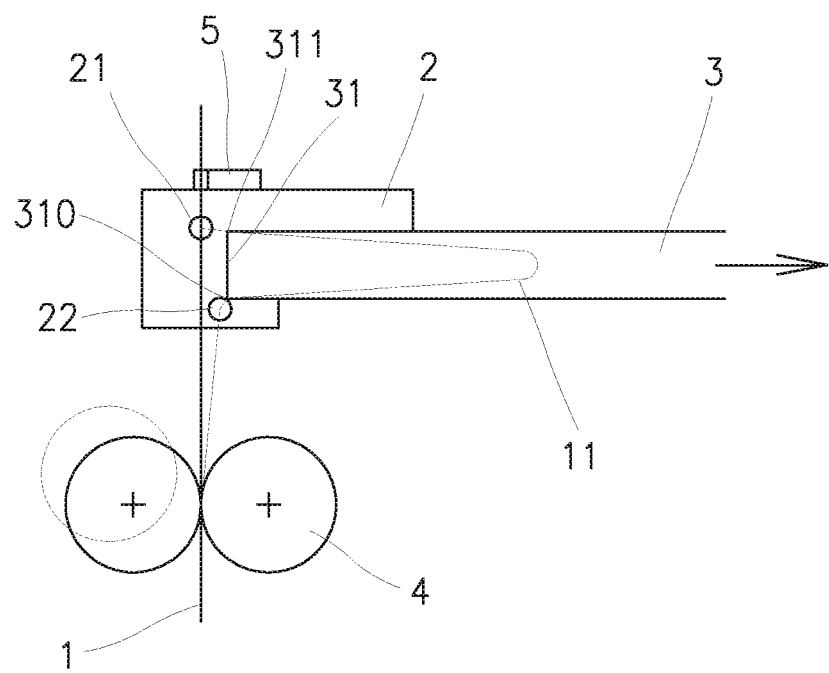
Figure 4:
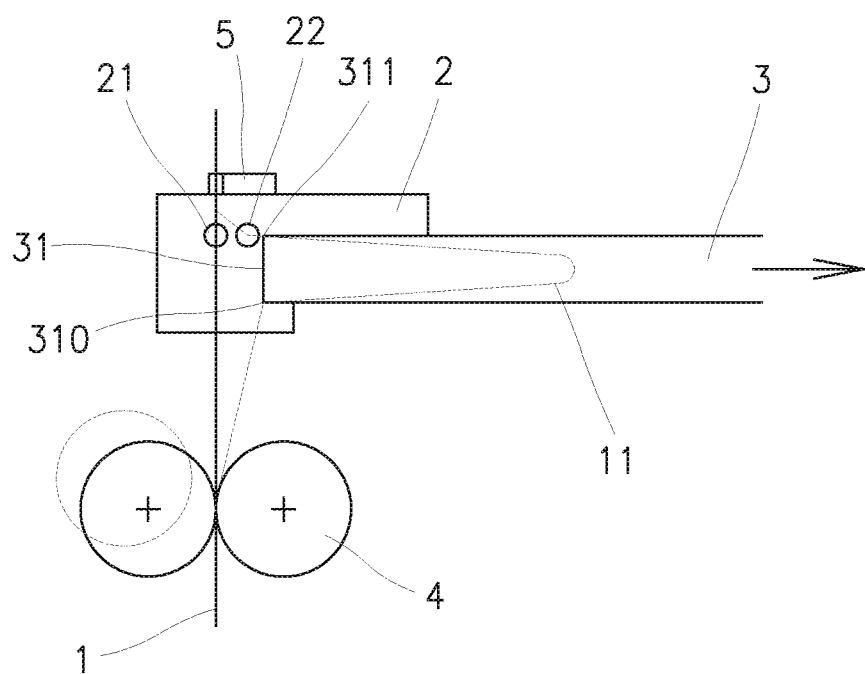

FIGS. 3 and 4 show simple modifications of the embodiments of FIGS. 1 and 2, whereby the behavior of the yarn 1 is detected again by a pair of detection zones 21, 22, which are suitably arranged with respect to the inlet 31 of the temporary storage device 3 of yarn 1. Also, both the straight yarn path and the deflected yarn path are indicated here, from which on the basis of the description of the embodiment in FIG. 1, it is clear which detection zone 21, 22 is assigned to which yarn path, or it is assigned to both yarn paths. Therefore it is obvious to the skilled person on the basis of the foregoing description how the information about the yarn 1 is sensed along the straight path and how the information about the yarn 1 is sensed along the deflected path. In the embodiment in FIG. 3, the lower detection zone 22 is assigned to the deflected yarn path in the region of the inlet edge 310 of the inlet 31 of the temporary storage device 3, the upper detection zone 21 being situated as in the embodiment of FIG. 1. In the embodiment of FIG. 4, the two detection zones 21, 22 are situated at the same horizontal level, the lower detection zone 22 being situated as in the exemplary embodiment of FIG. 2 and the upper detection zone 21 being shifted downwards compared to the embodiment in FIG. 2. In the embodiment in FIG. 4 the terms "upper" and "lower" detection zone 21, 22, are used, although it is evident that from the geometrical point of view, the two zones 21, 22 are situated side by side. This terminology, however, is appropriate for the consistency of the description.

In the embodiment of FIGS. 3 and 4, the control unit of the workstation (or of the section of the workstations or of the entire machine) also receives the information that the yarn 1 has left the temporary storage device 3, and the control unit, in case of need, adjusts accordingly the subsequent operating activity of the workstation to put the workstation into full production mode.

In principle, the embodiment according to FIGS. 1 to 4 the detection zones 21, 22 are used for sensing at least the presence, or, alternatively, also the quality and movement of yarn 1.

Figure 5:
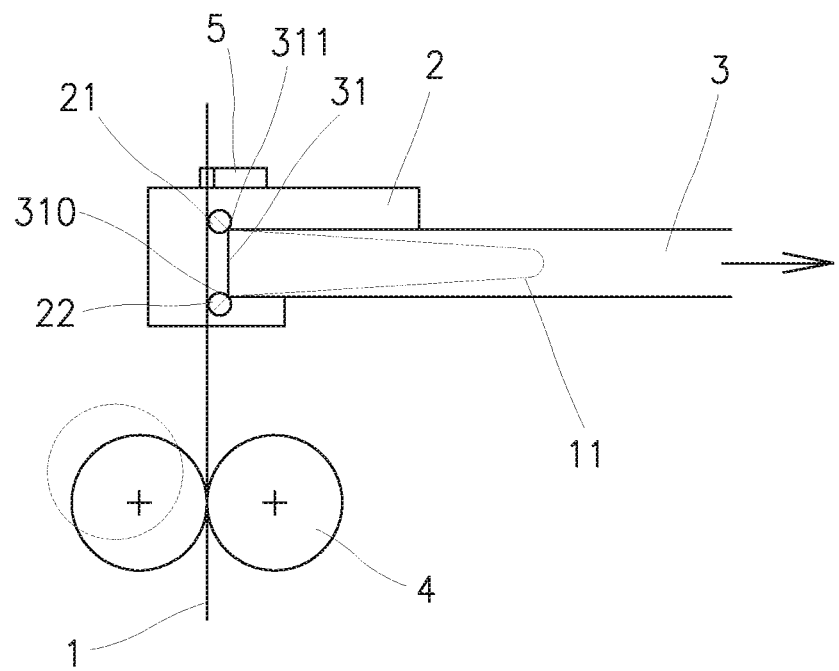

In another embodiment, FIG. 5 shows the use of the detection zones for sensing at least the movement of yarn 1, whereby the upper and lower detection zones 21, 22 are assigned to the upper and lower edges 311, 310 of the inlet 31 of the temporary storage device 3 and the two detection zones 21, 22 are assigned both to the straight yarn path 1 (solid line) and the deflected yarn path (dashed line). By detecting the movement of the yarn 1 relative to the individual detection zones 21, 22 it is determined at the workstation whether the temporary storage device 3 is filled or emptied, as is apparent to the skilled person from the foregoing description, and on the basis of this, the workstation is controlled by the control unit. Due to the small distance of the inlet 31 of the temporary storage device 3 from the yarn path, this arrangement is particularly advantageous for achieving high yarn suction reliability into the temporary storage device 3 of yarn 1.

It is obvious that, as to the detection zones 21, 22, it is possible to use even more than the two zones 21, 22 illustrated and described here. A common feature is the fact that the individual detection zones 21, 22 are arranged in defined positions with respect to the yarn path in different situations and states of yarn 1, which correspond to different situations and states at the workstation of the machine. Preferably, the detection zones 21, 22 etc., comprise at least one row of radiation sensitive elements, e.g., CCD or CMOS, but they can also include other sensing means, including analog sensing means, etc.

It is clear from the above that the individual detection zones 21, 22 are arranged in an order and spatial orientation corresponding to different situations at the workstation during measurement of different parameters of yarn 1, such as the presence and/or quality and/or movement of yarn 1. The individual detection zones 21, 22 are arranged in a common plane in different directions, or they are arranged in two or more planes and/or directions, e.g., in mutually perpendicular planes and directions to the movement of yarn 1.

Depending on the specific requirements and situations at the workstation, the system is configured such that the individual detection zones 21, 22 can be purposely and intentionally activated or, on the contrary, deactivated in the appropriate situations at the workstation, both during the production process, i.e. in the production of yarn and during non-production activities, e.g., when servicing operations are performed at the workstation, e.g., after a yarn break, or during spinning-in, etc.

Figure 6:
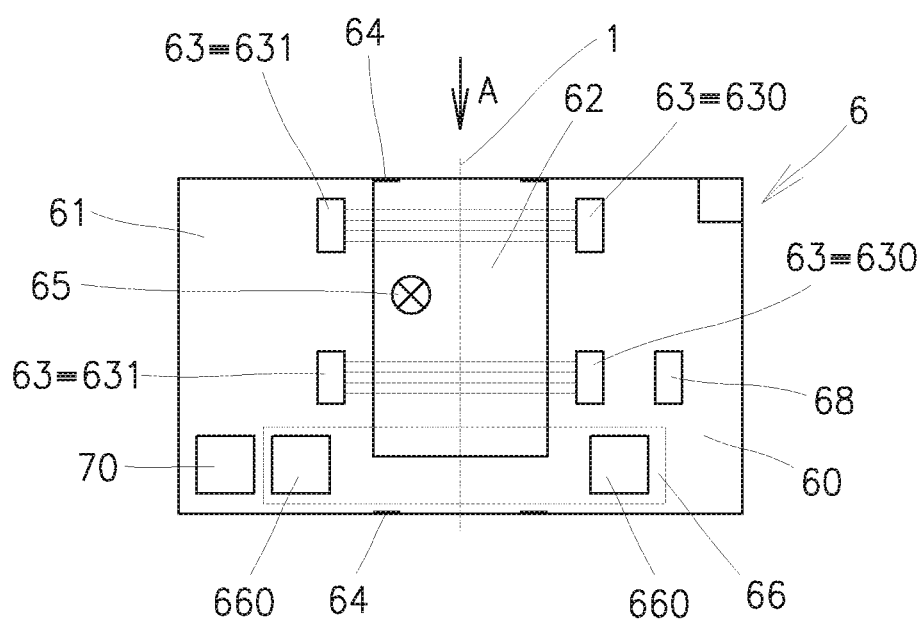
FIG. 6 shows a front view of a first exemplary embodiment of the device according to the invention, specifically the yarn sensor.
Figure 6A:
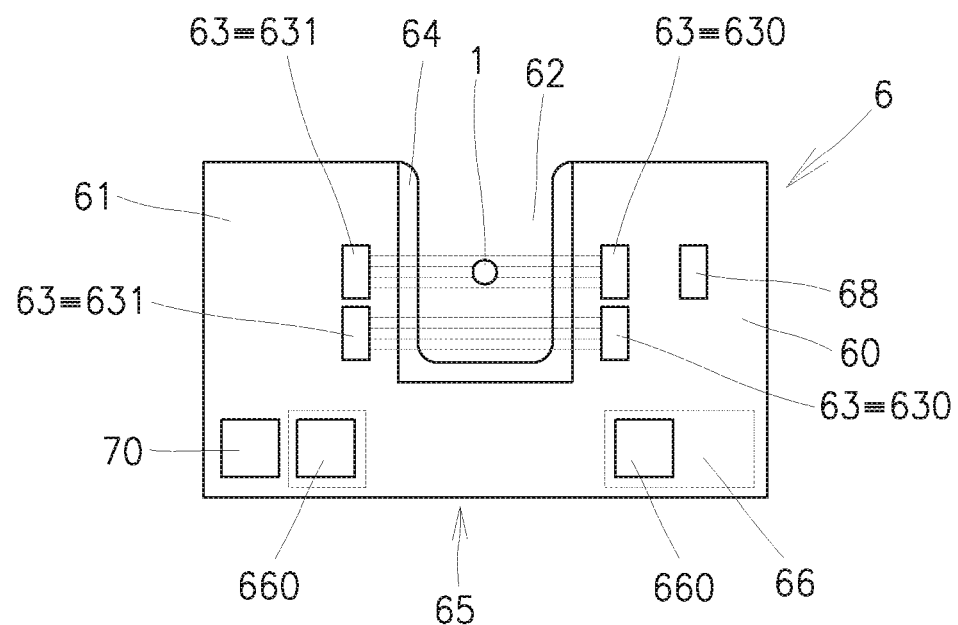
FIG. 6a shows a plan view (in the direction of arrow A of FIG. 6) of the first exemplary embodiment of the device according to the invention, specifically the yarn sensor.
Figure 7:
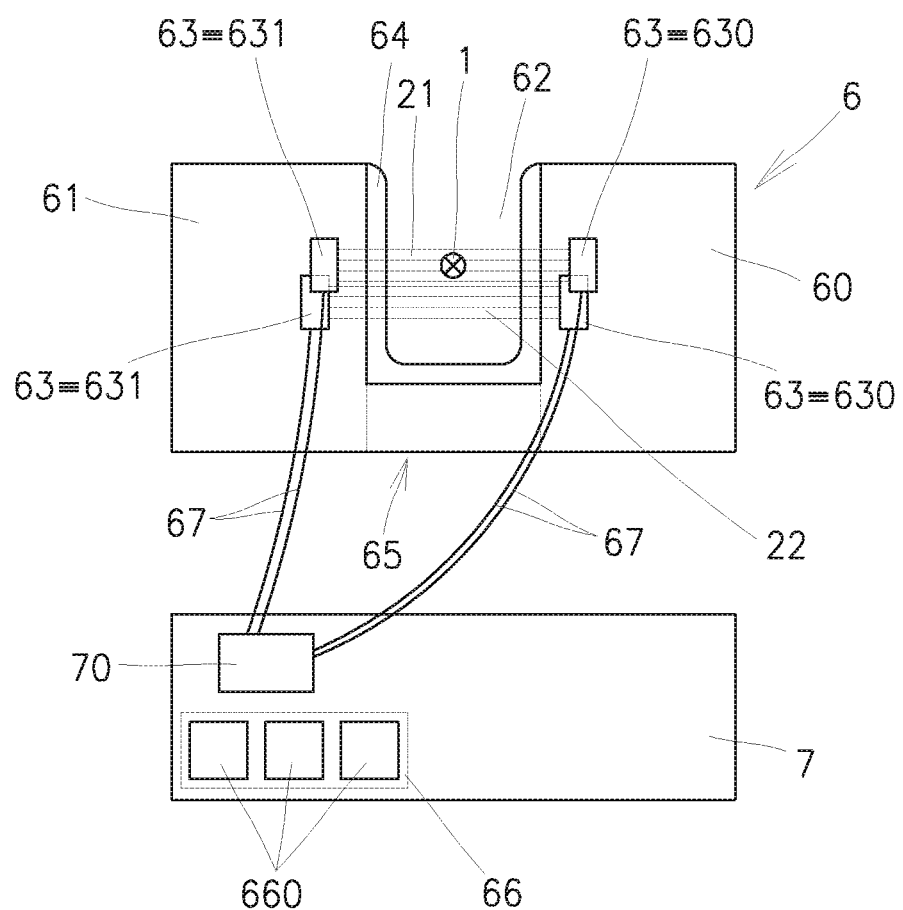
FIG. 7 shows a plan view of a second exemplary embodiment of the device according to the invention, specifically the yarn sensor, with a separated part.

FIGS. 6, 6a and 7 show an exemplary embodiment with an arrangement of the device for monitoring the yarn 1 according to the invention, specifically the yarn 1 sensor, which comprises a housing 6. The housing 6 comprises a pair of opposed parts 60, 61, between which there is a space 62 for the passage of yarn 1. In each of the parts 60, 61 elements 63 for sensing yarn 1 are arranged in the detection zones 21, 22, whereby these elements are formed by suitable sensors of the presence and/or quality of yarn, whether it be capacitance, optical or other suitable sensors. In the shown exemplary embodiment, optical yarn sensors are used which have transmitters 630 of radiation in one part 60, 61, i.e. on one side of the detection zones 21, 22, while in the second part 60, 61 of the housing 6, i.e. on the other side of the detection zones 21, 22, they have receivers 631 of radiation. In the exemplary embodiment in FIG. 6a, which is a plan view, the elements 63 for sensing yarn 1 in the detection zones 21, 22 and the two detection zones 21, 22 overlap (because they are above one another). In the embodiment in FIG. 7, the elements 63 for sensing yarn 1 in the detection zones 21, 22 and the two detection zones 21, 22 are arranged with partial overlap in a plan view. In another exemplary embodiment, the elements 63 are mutually arranged in the required positions, as is described in greater detail in the previous parts of the description and shown in FIGS. 1 to 5.

Since the embodiment according to FIGS. 6, 6a, 6b and 7 is intended to provide the detection zones 21, 22 at the inlet 31 of the temporary storage device 3 of yarn 1, a through opening 65 into the space 62 for the yarn passage is formed in the rear wall of the housing 6 and to the through opening 65 is assigned the inlet 31 of the yarn temporary storage device 3, (not shown in FIGS. 6, 6a, 6b and 7). The elements 63 for sensing yarn 1 in the detection zones 21, 22 are arranged in the desired positions in the housing 6 with respect to the opening 65, i.e., also with respect to the inlet 31 of the temporary storage device 3 of yarn 1.

Figure 6B:
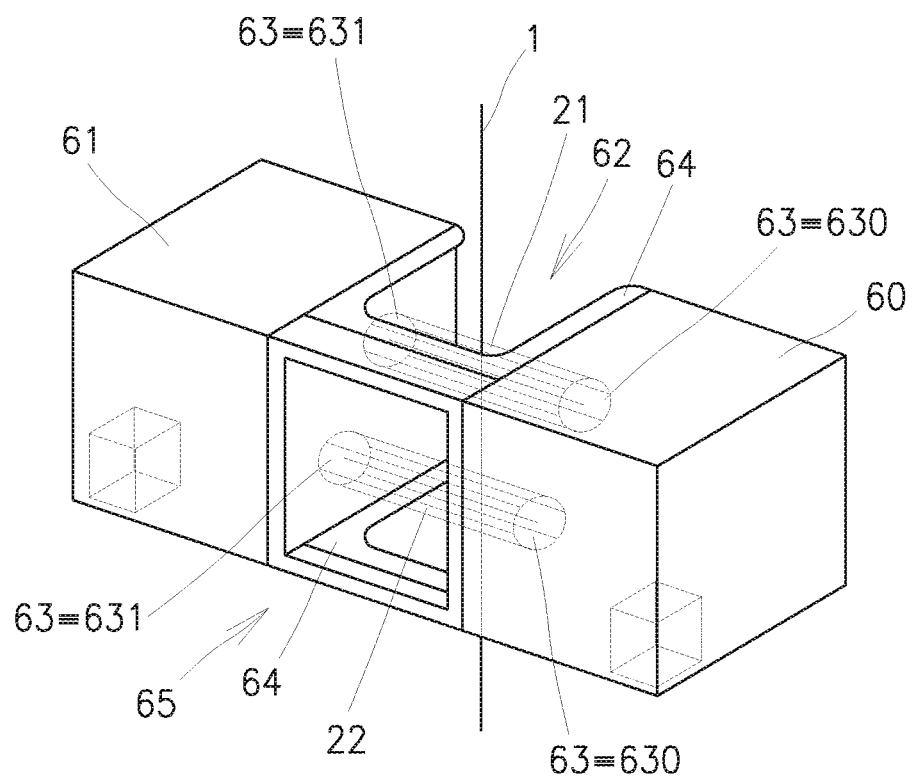

The elements 63 for sensing yarn 1 in the detection zones 21, 22 are, for example in FIGS. 6, 6a and 6b, arranged on a circuit board 70 ensuring the functionality of the elements 63, or the elements 63 for sensing yarn 1 in the detection zones 21, 22 are mounted in the housing 6 separately and are coupled by means of lines 67 to the circuit board 70 ensuring the functionality of the elements, as shown in FIG. 7, and/or are coupled by means of the lines 67 directly to evaluation electronics 66.

The elements 63 for sensing yarn 1 in the detection zones 21, 22 are further coupled to the evaluation electronics 66, which is arranged either directly in the housing 6, see FIGS. 6, 6a and 6b, or separately or directly on the circuit board 70, or the evaluation electronics 66 is arranged in a separate housing 7, see FIG. 7, or in the unillustrated example of embodiment partly in the housing 6 and partly in a separate housing 7. A separate housing 7 is advantageous if there is little room for all the required elements of the device according to the invention directly at the workstation in the area of installation of the detection zones. The evaluation of the detection zones 21, 22 takes place either directly in the housing 6 or at a remote location, i.e. in the separate housing 7, or takes place partly in the housing 6 and partly at a remote location, i.e. in the separate housing 7.

Depending on the type of the elements 63 for sensing yarn 1 in the detection zones 21, 22 lines 67 connecting the elements 63 to the circuit board 70 are made, whether they are made as a metallic data line or it is made by means of optical fibers, etc.

As shown in FIGS. 6, 6a, 6b and 7, the evaluation of the signal of the elements 63 for sensing yarn 1 in the detection zones 21, 22 is performed by one or two or even more signal processors 660. The results of the evaluation of the state of the detection zones 21, 22 are released through one or two digital outputs, or by one or two data lines (CAN bus, bit serial, another data transfer system). In an unillustrated embodiment, the housing 6 or the separate housing 7 is provided with an optical information element, e.g., an LED whose operation, i.e. visual signaling, corresponds to the detected state of the detection zones.

Accommodated in the housing 6 in the embodiment shown is also a power supply 68, e.g., 24V/5V, for the elements 63 for sensing yarn 1 in the detection zones 21, 22 and, if necessary, for the other elements in the housing 6.

The elements 63 for sensing yarn 1 in the detection zones 21, 22 and the means for their operation are either located separately in the housing 6, i.e. without other means of controlling the workstation (the housing 6 is intended to accommodate only the elements 63 and their support and evaluation means), or they are arranged in the housing 6 together with other means of controlling of the workstation.

At least at the upper and lower edges of the space 62 for the passage of yarn 1, the housing 6 is provided with yarn guides 64 which are made of a durable material, e.g., ceramics, or are provided with a durable surface in the form of a coating, etc. Since during the operation of the device at the inlet 31 of the temporary storage device 3 of yarn 1 there are also major changes in the direction of the yarn 1, the yarn guide in the unillustrated exemplary embodiment is assigned also to the inlet 31 of the temporary storage device 3 of yarn 1. In other words, it is situated in the region of the opening 65 for the inlet 31 of the temporary storage device 3 of yarn 1.

From the point of view of production, it is advantageous if the housing 6 and/or the separate housing 7 is formed by any of the methods for plastic processing, for example, as a plastic molded piece or plastic injection molding object, etc. From the point of view of mounting, it is suitable if the circuit board or circuit boards in the housing 6 and/or in the separate housing 7 is/are fastened by screws and/or clamps and/or clips and/or are cast in a suitable sealing compound. The housing can be also prepared by the technique HotMelt together with the elements accommodated in the housing.

The method and device according to the invention can be used on textile machines to control the position or changes in the position of a textile formation or the speed of the textile formation movement or changes in the speed of its movement.

Modifications and variations can be made to the embodiments illustrated or described herein without departing from the scope and spirit of the invention as set forth in the appended claims.

The invention claimed is:

1. A device for contactless measurement of one or more parameters of a linear textile formation, comprising:
a yarn sensor, the yarn sensor further comprising at least two mutually independent and spaced-apart detection zones for one or a combination of the parameters of yarn presence, yarn movement, or yarn quality; and
wherein the detection zones are arranged in defined spaced-apart positions relative to at least two different yarn paths of the yarn at a workstation that depend on changed states of the yarn at the workstation so that for each of the different yarn paths at least one of the parameters is measurable in at least one of the detection zones.

2. The device according to claim 1, wherein the individual detection zones are arranged in the defined positions relative to a straight yarn path and to a deflected yarn path at the workstation.

3. The device according to claim 1, wherein at least two of the different yarn paths are assigned to at least one of the detection zones.

4. The device according to claim 1, wherein the detection zones are arranged in an order and spatial orientation relative to the different yarn paths caused by different yarn production situations at the workstation.

5. The device according to claim 1, wherein with respect to a direction of yarn movement, the detection zones are arranged in a common vertical or horizontal plane or in different vertical or horizontal planes.

6. A yarn manufacturing textile machine comprising the device according to claim 1.

7. A device for contactless measurement of one or more parameters of a linear textile formation, comprising:
a yarn sensor, the yarn sensor further comprising at least two mutually independent detection zones for one or a combination of the parameters of yarn presence, yarn movement, or yarn quality;
wherein the detection zones are arranged in defined positions relative to at least two different yarn paths of the yarn at a workstation that depend on changed states of the yarn at the workstation so that at least one of the parameters is measurable in each of the detection zones; and
wherein the yarn sensor comprises a pair of opposed parts with a space therebetween for passage of the yarn, for each of the detection zones, detection elements are mounted in each of the parts and are coupled to at least one circuit board and to an electronic evaluation device.

8. The device according to claim 7, wherein the detection elements are coupled with the circuit board and the electronic evaluation device via lines.

9. The device according to claim 7, wherein the electronic evaluation device comprises a signal processor, a digital output, and a data line.

10. The device according to claim 7, wherein the opposed parts comprise a housing, the detection elements comprising optical yarn sensors having a transmitter in the housing at a side of the passage and a receiver in the housing at an opposite side of the passage.

11. The device according to claim 10, wherein the housing comprises a through opening in a rear wall thereof assigned to an inlet of a temporary yarn storage device, the detection elements arranged in the housing so that at least one of the detection zones is configured to measure at least one of the parameters of the yarn passing through the opening and into the temporary yarn storage device.

12. The device according to claim 10, wherein the electronic evaluation devices are arranged in the housing.

13. The device according to claim 10, wherein the electronic evaluation devices are arranged in a separate housing remote from the housing having the detection elements therein.

14. The device according to claim 13, further comprising an optical information element configured with one or both of the housing and the separate housing.

15. The device according to claim 13, wherein one or both of the housing and the separate housing are formed from a plastic molded piece, a plastic injection molding object, or a hot-melt formed object, and wherein the circuit boards, detection elements, and electronic evaluation devices fastened by screws, clamps, clips, or a sealing compound in the housing.

16. The device according to claim 10, wherein the electronic evaluation devices are arranged partly in the housing with the detection elements and partly within a separate housing remote from the housing having the detection elements therein.

17. The device according to claim 10, further comprising workstation control devices in the housing.

18. The device according to claim 10, wherein the housing comprises yarn guides configured with the housing.

* * * * *